United States Patent
Yao et al.

(10) Patent No.: US 11,892,443 B2
(45) Date of Patent: Feb. 6, 2024

(54) MICRO-ENVIRONMENT CONTROLLABLE TEMPERATURE AND HUMIDITY SYSTEM AND METHOD FOR EVALUATING HEAT AND HUMIDITY COMFORT LEVEL OF TEXTILES

(71) Applicant: The Hong Kong Research Institute of Textiles and Apparel Limited, Hong Kong (CN)

(72) Inventors: Lei Yao, Hong Kong (CN); Xiao Liao, Hong Kong (CN); Siyu Lin, Hong Kong (CN)

(73) Assignee: THE HONG KONG RESEARCH INSTITUTE OF TEXTILES AND APPAREL LIMITED, Kowloon (HK)

( * ) Notice: Subject to any disclaimer, the term of this patent is extended or adjusted under 35 U.S.C. 154(b) by 1162 days.

(21) Appl. No.: 16/480,102

(22) PCT Filed: Feb. 28, 2017

(86) PCT No.: PCT/CN2017/075206
§ 371 (c)(1),
(2) Date: Jul. 23, 2019

(87) PCT Pub. No.: WO2018/152857
PCT Pub. Date: Aug. 30, 2018

(65) Prior Publication Data
US 2019/0376945 A1 Dec. 12, 2019

(30) Foreign Application Priority Data
Feb. 22, 2017 (CN) .......................... 201710098708.9

(51) Int. Cl.
*A61M 16/16* (2006.01)
*A61B 5/24* (2021.01)
(Continued)

(52) U.S. Cl.
CPC ........... *G01N 33/36* (2013.01); *A61M 16/161* (2014.02); *F24F 11/0001* (2013.01);
(Continued)

(58) Field of Classification Search
CPC .. A61M 16/161; A61B 5/4815; A47C 21/042; A47C 21/044; A47C 21/048
See application file for complete search history.

(56) References Cited

U.S. PATENT DOCUMENTS 7,877,827 B2 * 2/2011 Marquette ............. F24H 3/0429
5/652.2
2005/0121530 A1 6/2005 Song
(Continued)

FOREIGN PATENT DOCUMENTS

CN 1971268 A 5/2007
CN 101737903 A 6/2010
(Continued)

OTHER PUBLICATIONS

International Search Report dated Aug. 3, 2017 issued in corresponding PCT/CN2017/075206 application (3 pages).
(Continued)

*Primary Examiner* — Daniel J Colilla
(74) *Attorney, Agent, or Firm* — Millen, White, Zelano & Branigan, P.C.; William F. Nixon

(57) ABSTRACT

A micro-environment controllable temperature and humidity system evaluates heat and humidity comfort level of textiles. The system includes a bed-shaped partitioned platform having one or more non-temperature and humidity-controllable sections and one or more temperature and humidity controllable sections. One or more temperature and humidity control machine is in communication with the one or more temperature and humidity control sections for supplying air with a pre-set temperature and humidity. A central (Continued)

controller electrically is connected to the one or more temperature and humidity control machines. The micro-environment controllable temperature and humidity system can perform partitioned control on the temperature and humidity in a micro-environment during sleep, and is used for studying the influence of the temperature and humidity on the comfort level of different regions of a subject.

9 Claims, 3 Drawing Sheets

(51) Int. Cl.

| | | |
|---|---|---|
| A47C 21/04 | (2006.01) | |
| G01N 33/36 | (2006.01) | |
| F24F 11/62 | (2018.01) | |
| F24F 11/00 | (2018.01) | |
| G05D 27/02 | (2006.01) | |
| A61M 16/00 | (2006.01) | |
| F24F 110/10 | (2018.01) | |
| F24F 110/20 | (2018.01) | |
| F24F 120/20 | (2018.01) | |

(52) U.S. Cl.
CPC .......... *F24F 11/0008* (2013.01); *F24F 11/62* (2018.01); *G05D 27/02* (2013.01); *A47C 21/04* (2013.01); *A61M 2016/0027* (2013.01); *F24F 2110/10* (2018.01); *F24F 2110/20* (2018.01); *F24F 2120/20* (2018.01); *G01N 2333/435* (2013.01)

(56) References Cited

U.S. PATENT DOCUMENTS

| | | | | |
|---|---|---|---|---|
| 2007/0251016 A1* | 11/2007 | Feher | ............... | A47C 7/748 |
| | | | | 455/39 |
| 2011/0115635 A1* | 5/2011 | Petrovski | ............ | A47C 31/008 |
| | | | | 340/584 |
| 2011/0258778 A1* | 10/2011 | Brykalski | ............ | A61G 7/057 |
| | | | | 5/421 |
| 2012/0210513 A1 | 8/2012 | Chestakov et al. | | |
| 2016/0136385 A1* | 5/2016 | Scorcioni | ............ | A61B 5/4812 |
| | | | | 600/26 |

FOREIGN PATENT DOCUMENTS

| | | |
|---|---|---|
| CN | 102349758 A | 2/2012 |
| CN | 203010838 U | 6/2013 |
| CN | 103885508 A | 6/2014 |
| CN | 203802442 U | 9/2014 |
| CN | 105136847 A | 12/2015 |
| CN | 106361059 A | 2/2017 |
| EP | 2496996 B1 | 3/2014 |
| JP | 2009243724 A | 10/2009 |
| JP | 2017-6359 A | 1/2017 |
| WO | 05120295 A1 | 12/2005 |
| WO | 16155240 A1 | 10/2016 |

OTHER PUBLICATIONS

English Abstract of CN 101737903 A published Jun. 16, 2010.
English Abstract of CN 102349758 A published Feb. 15, 2012.
English Abstract of CN 203010838 U published Jun. 19, 2013.
English Abstract of CN 103885508 A published Jun. 25, 2014.
English Abstract of CN 203802442 U published Sep. 3, 2014.
English Abstract of JP 2017-006359 A published Jan. 12, 2017.
English Abstract of CN 106361059 A published Feb. 1, 2017.
Supplementary EP search report in corresponding EP 17 89 7337 dated Jul. 9, 2020 (pp. 1-8).

* cited by examiner

Temperature:

☐ 1———☐ 2———☐ 3———☐ 4———☐ 5———☐ 6———☐ 7
Very Hot                    Neutral                     Very Cold Relative Humidity:

☐ 1———☐ 2———☐ 3———☐ 4———☐ 5———☐ 6———☐ 7
Very Wet                    Neutral                     Very Dry Overall Comfort:

☐ 1———☐ 2———☐ 3———☐ 4———☐ 5———☐ 6———☐ 7
Highly Uncomfortable        Neutral                 Highly Comfortable

MICRO-ENVIRONMENT CONTROLLABLE TEMPERATURE AND HUMIDITY SYSTEM AND METHOD FOR EVALUATING HEAT AND HUMIDITY COMFORT LEVEL OF TEXTILES

TECHNICAL FIELD

The present disclosure relates to the field of sleep environment control, and more particularly to a micro-environment controllable temperature and humidity system and method for evaluating heat and humidity comfort level of textiles.

BACKGROUND ART

Sleep plays a vital role in human health and many factors can affect the comfort level of sleep, such as temperature and humidity, bedding, and the material of pajamas tightly attached to our skin during sleep. With the increase of life pressure, the comfort level of sleep is increasingly drawing attentions of people, and more and more people are pursuing bed textiles with a high comfort level. In view of a complex sensory system of human beings, the test results of physical test methods for bed textiles at this stage do not truly reflect the real comfort level of the human body. For test method experiments involving the participation of a human body, sleep experiments should be performed under controllable temperature and humidity conditions, so that the other factors, other than textiles, that affect the comfort level are excluded. However, many sleep laboratory devices only control the temperature and humidity of the environment to study the sleep heat comfort level of textiles, but they cannot regulate the temperature and humidity of the micro-environment around the human body. However, the temperature and humidity of the micro-environment are the main factors directly affecting human sleep. On the other hand, some devices for the micro-environment are not suitable for the study on the heat and humidity comfort level of textiles. In addition, importantly, due to the structural problem of the human body, the blood flow and the skin temperature of different parts of the body of each person vary greatly, for example, the skin temperature of the limbs farther from the heart is very different from that of the trunk, and the comfort feeling of each part is also very different.

SUMMARY

The technical problem to be solved by the present disclosure is to provide, with regard to the prior art in which only the temperature and humidity of an environment can be controlled, a micro-environment controllable temperature and humidity system and method for evaluating the sleep heat and humidity comfort level of textiles, which can realize the partitioned temperature and humidity control of a micro-environment of a subject, for studying the comfort level of the textiles located in different regions of the subject.

The technical solution adopted by the present disclosure to solve the technical problem thereof is: providing a system for evaluating heat and humidity comfort level of textiles proximal a subject during sleeping, the system comprising:
 a bed-shaped partitioned platform comprising one or more non-temperature and humidity-controllable sections and one or more temperature and humidity controllable sections which define a micro environment therein;
 one or more temperature and humidity control machines in communication with the one or more temperature and humidity control sections respectively for supplying air with a pre-set temperature and humidity; and
 a central controller electrically connected to the one or more temperature and humidity control machines.

Preferably, the system may further comprise: a heat and humidity comfort level detection sensing apparatus (5) comprising a physiological index sensor (51) for collecting physiological data, and an acceleration sensor (52) for collecting data of the body position and the activity amount associated with a change of body position of a subject during sleep on the platform; and
 one or more sleep temperature and humidity sensors (8) for collecting the micro-environment temperature and humidity of various parts of the subject during sleep.

Preferably, the system may further comprise a controllable temperature and humidity test chamber, wherein an air outlet and an air return inlet are respectively arranged at the top and bottom of the controllable temperature and humidity test chamber, and a diffuser plate is mounted below the air outlet; and the bed-shaped partitioned platform may be arranged in the controllable temperature and humidity test chamber, and the air return inlet may be further arranged at the bottom of the bed-shaped partitioned platform.

Preferably, the system may further comprise a test chamber temperature and humidity control machine electrically connected to the central controller, air emitted from the test chamber temperature and humidity control machine may pass through the air outlet and then enter the controllable temperature and humidity test chamber through the diffuser plate.

Preferably, a test chamber temperature and humidity sensor may be further arranged at the air outlet, and the test chamber temperature and humidity sensor may be electrically connected to the central controller.

Preferably, the one or more temperature and humidity control machines may be respectively in communication with one or more ventilation pipelines, and air outlets of the one or more ventilation pipelines may respectively correspond to and be in communication with one or more lower-layer air inlets arranged at the bottom of the bed-shaped partitioned platform, and the one or more lower-layer air inlets may be respectively in communication with one or more section diffusers arranged thereabove; and
 a heat dissipation polyester layer may be arranged close to and above the one or more section diffusers, an upper-layer return air passage may be arranged above the heat dissipation polyester layer, and the upper-layer return air passage may be in communication with the controllable temperature and humidity test chamber.

Preferably, air inlets of the one or more ventilation pipelines may be respectively provided with one or more temperature sensors, and the one or more temperature sensors may be respectively electrically connected to the central controller.

Preferably, a connection opening may be arranged on a side wall of the controllable temperature and humidity test chamber, and data cables of the physiological index sensor and the acceleration sensor may be connected to an external computer through the connection opening; and
 a ventilation window may be further arranged on the side wall of the controllable temperature and humidity test chamber, and a ventilation fan may be arranged in the ventilation window.

The present disclosure also provides a micro-environment controllable temperature and humidity method for evaluating heat and humidity comfort level of textiles proximal a subject during sleeping, the method comprising:

disposing a test textile on a bed-shaped partitioned platform;

arranging one or more sleep temperature and humidity sensors respectively under the surface of a mattress of the bed-shaped partitioned platform and in a corresponding position in the textile;

arranging a physiological index sensor and an acceleration sensor on the body of a subject;

setting and adjusting a controllable temperature and humidity test chamber and the bed-shaped partitioned platform to a pre-set temperature and humidity, and then allowing the subject to enter the controllable temperature and humidity test chamber;

completing a heat and humidity comfort level psychological evaluation questionnaire and thereafter allowing the subject to lie on the bed-shaped partitioned platform and entering a sleep state;

monitoring the sleep state of the subject all night and collecting data;

the subject filling in the heat and humidity comfort level psychological evaluation questionnaire and a sleep quality psychological evaluation questionnaire after a predetermined time period; and analyzing the data obtained from performing the previous steps, and subjectively and objectively evaluating the test textile.

Preferably, the analyzing data and evaluating the test textile may further comprise:

evaluating a heat and humidity transfer performance and a material uniformity of the test textile according to physical level data obtained by the one or more sleep temperature and humidity sensors, thereby evaluating an objective heat and humidity comfort level of the test textile;

evaluating a subjective heat comfort level of the test textile according to psychological level data obtained from all the questionnaires;

evaluating the sleep quality according to physiological data obtained by the physiological index sensor and the acceleration sensor, thereby evaluating the objective heat and humidity comfort level of the test textile; and comprehensively evaluating a sleep heat and humidity comfort level of the test textile according to different data and evaluation results in the previous steps, and the steps before comprehensively evaluating may be executed in an arbitrary order.

The beneficial effects of the present disclosure line in that the micro-environment controllable temperature and humidity system can perform partitioned control on the temperature and humidity in a micro-environment during sleep, and is used for studying the influence of the temperature and humidity on the comfort level of different regions of a subject. The method of the present disclosure evaluates the sleep heat and humidity comfort level of textiles in three levels of physics, physiology and psychology, and performs subjective and objective test evaluations on the textiles, thereby making up for the defects in the existing methods that the sleep heat and humidity comfort level of textiles cannot be comprehensively evaluated.

BRIEF DESCRIPTION OF THE DRAWINGS

The present disclosure will be further described below in conjunction with the drawings and embodiments, in which.

DETAILED DESCRIPTION OF EMBODIMENTS

For a better understanding of the technical features, objects, and advantages of the present disclosure, the detailed description of embodiments of the present disclosure will be described in detail with reference to the drawings.

Figure 1:
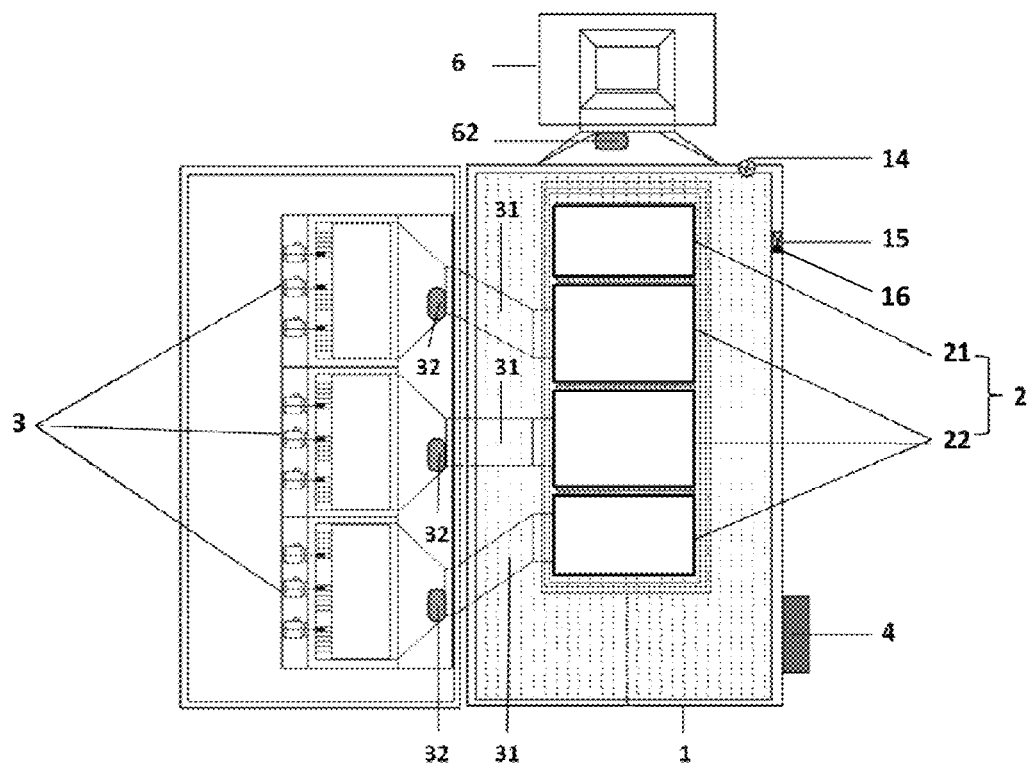
FIG. 1 is a structural schematic top view of a preferred embodiment of a micro-environment controllable temperature and humidity system for evaluating heat and humidity comfort level of textiles according to the present disclosure.
Figures 4, 5:
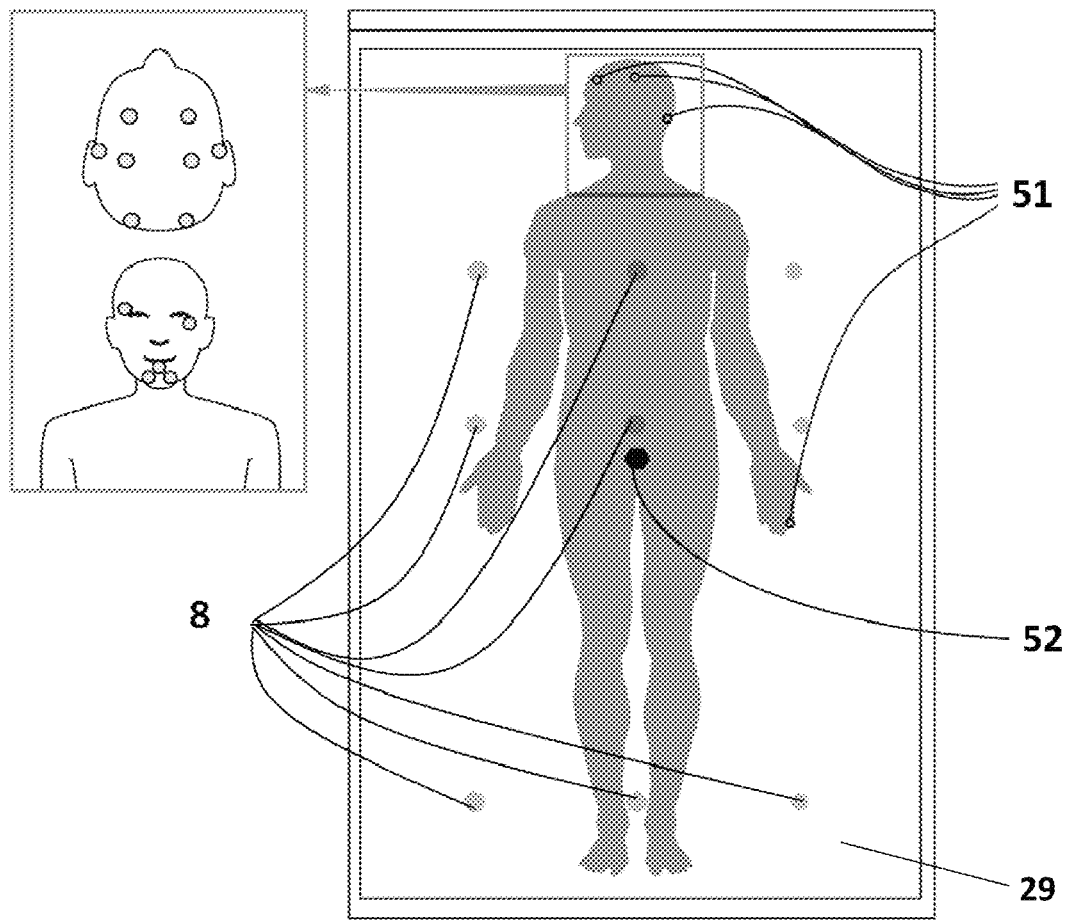
FIG. 4 is a schematic diagram of setting a sensor for collecting physical and physiological data in a micro-environment controllable temperature and humidity method for evaluating heat and humidity comfort level of textiles according to the present disclosure.
FIG. 5 illustrates the evaluation criteria for the heat and humidity comfort level psychological evaluation questionnaire according to the present disclosure.

FIG. 1 is a structural schematic top view of a preferred embodiment of a micro-environment controllable temperature and humidity system for evaluating heat and humidity comfort level of textiles according to the present disclosure. The micro-environment controllable temperature and humidity system comprises: a bed-shaped partitioned platform 2, which comprises one or more non-temperature and humidity-controllable sections 21 and one or more temperature and humidity controllable sections 22; one or more temperature and humidity control machines 3 being in communication with the one or more temperature and humidity control sections 22 respectively for supplying air with a pre-set temperature and humidity; and a central controller 4 electrically connected to the one or more temperature and humidity control machines 3; a heat and humidity comfort level detection sensing apparatus (as shown in FIG. 4) comprising a physiological index sensor (as shown in FIG. 4) for collecting physiological data and an acceleration sensor (as shown in FIG. 4) for collecting data of the body position and activity amount associated with a change of body position of a human body during sleep on the platform. The one or more temperature and humidity control machines 3 are respectively in communication with one or more temperature and humidity control sections 22 through one or more ventilation pipelines 31. Fire-retardant and sound-absorbing materials are respectively provided in the one or more ventilation pipelines 31.

Air inlets of the one or more ventilation pipelines 31 are respectively provided with one or more temperature sensors 32, and the one or more temperature sensors 32 are respectively electrically connected to the central controller 4. A connection opening 14 is arranged on a side wall of the controllable temperature and humidity test chamber 1, and data cables of the physiological index sensor and the acceleration sensor are connected to an external computer through the connection opening 14; and a ventilation window 15 is further arranged on the side wall of the controllable temperature and humidity test chamber 1, and a ventilation fan 16 is arranged in the ventilation window 15.

The micro-environment controllable temperature and humidity system further comprises one or more sleep temperature and humidity sensors (as shown in FIG. 4) for collecting the micro-environment temperature and humidity of various parts of the human body during sleep.

Figure 2:
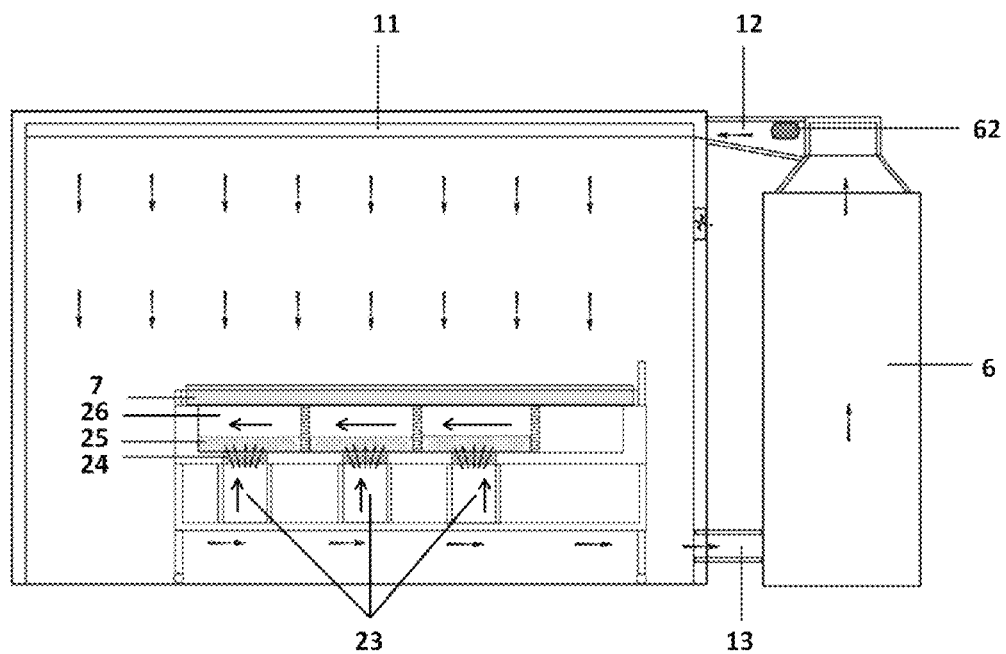
FIG. 2 is a structural schematic side view of a preferred embodiment of a micro-environment controllable temperature and humidity system for evaluating heat and humidity comfort level of textiles according to the present disclosure.

FIG. 2 is a structural schematic side view of a preferred embodiment of a micro-environment controllable temperature and humidity system for evaluating heat and humidity comfort level of textiles according to the present disclosure. The micro-environment controllable temperature and humidity system further comprises a controllable temperature and humidity test chamber 1, and an air outlet 12 and an air return inlet 13 are respectively arranged at the top and bottom of the controllable temperature and humidity test chamber 1, and a diffuser plate 11 is mounted below the air outlet 12.

The bed-shaped partitioned platform 2 is arranged in the controllable temperature and humidity test chamber 1, and the air return inlet 13 is further arranged at the bottom of the bed-shaped partitioned platform 2.

The micro-environment controllable temperature and humidity system further comprises a test chamber temperature and humidity control machine 6 electrically connected to the central controller 4, and air emitted from the test chamber temperature and humidity control machine 6 passes through the air outlet 12 and then enters the controllable temperature and humidity test chamber 1 through the diffuser plate 11. A test chamber temperature and humidity sensor 62 is further arranged at the air outlet 12, and the test chamber temperature and humidity sensor 62 is electrically connected to the central controller 4.

One or more temperature and humidity control machines 3 are respectively in communication with one or more ventilation pipelines 31, and air outlets of the one or more ventilation pipelines 31 respectively correspond to and are in communication with one or more lower-layer air inlets 23 arranged at the bottom of the bed-shaped partitioned platform 2, and the one or more lower-layer air inlets 23 are respectively in communication with one or more section diffusers 24 arranged thereabove; and a heat dissipation polyester layer 25 is arranged close to and above the one or more section diffusers 24. An upper-layer return air passage 26 is arranged above the heat dissipation polyester layer 25, and the upper-layer return air passage 26 is in communication with the controllable temperature and humidity test chamber 1.

In a preferred embodiment, the bed-shaped partitioned platform 2 is mounted in the center of the controllable temperature and humidity system test chamber 1, and the diffuser plate 11 at the top of the controllable temperature and humidity system test chamber 1 is a uniformly hole-shaped diffuser plate that completely covers the entire test chamber. A heat-resistant and cold-resistant stainless steel plate is arranged inside the wall body of the test chamber; and a wall body thermal insulation layer thereof has a double-layer structure, comprising a thermal insulation layer and a heat insulation and sound insulation layer. The air outlet 12 of the test chamber is mounted above the uniformly hole-shaped diffuser plate, and an air guide plate can be adjusted and set during the experiment so as to control the air speed. Preferably, the speed of the air when reaching the bed-shaped micro-environment controllable test platform does not exceed 0.2 m/s. The air return inlet 13 is mounted below the bed-shaped partitioned platform 2, a lower end of the air return inlet 13 is 30 cm higher than the ground, and the noise in the test chamber should not exceed 45 dB.

In a preferred embodiment, one or more non-temperature and humidity-control sections 21 are a head section, and one or more temperature and humidity control sections 22 are three independent sections, namely a chest section, a crotch section, and a lower limb section. The head section has no temperature or humidity control, whereas the chest section, the crotch section and the lower limb section are all provided with a controllable micro-environmental temperature and humidity apparatus, and are divided into upper and lower layers of ventilation sections, and three section diffusers 24 and large-aperture heat dissipation polyester materials are correspondingly arranged in the middle.

The central controller 4 is further externally connected to a touch control panel, and can independently control the three independent temperature and humidity control sections of the bed-shaped platform and the temperature and humidity of the test chamber through the touch control panel, and can further measure and obtain the temperature and humidity of a local section according to a temperature and humidity sensor 32 and a test chamber temperature and humidity sensor 62, and respectively and automatically perform the linear temperature and humidity compensation correction by using a temperature and humidity control machine 3 and a test chamber temperature and humidity control machine 6.

Figure 3:
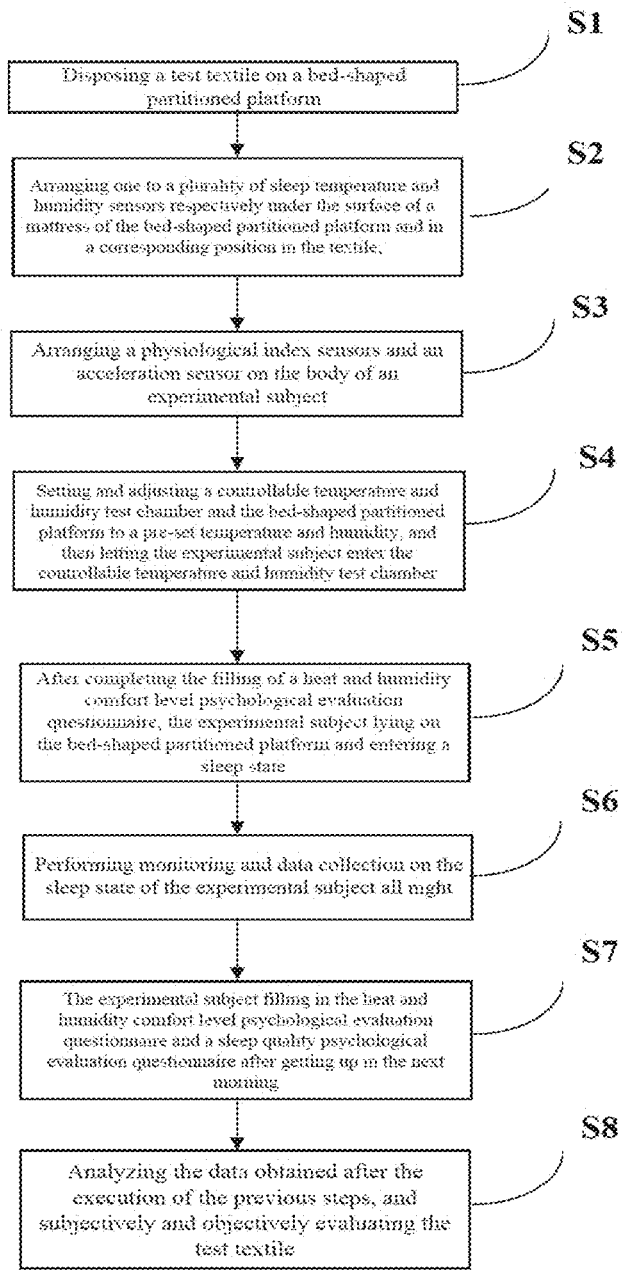
FIG. 3 is a schematic flow diagram of a preferred embodiment of a micro-environment controllable temperature and humidity method for evaluating heat and humidity comfort level of textiles according to the present disclosure.

FIG. 3 is a schematic flow diagram of a preferred embodiment of a micro-environment controllable temperature and humidity method for evaluating heat and humidity comfort level of textiles according to the present disclosure. The micro-environment controllable temperature and humidity method comprises the steps of:

S1, disposing a test textile on a bed-shaped partitioned platform 2, if the test textile is a quilt, the quilt of a control group can be directly replaced, and if it is a bed sheet, it can be directly laid on a mattress.

S2, arranging one or more sleep temperature and humidity sensors 8 respectively under the surface of a mattress 29 of the bed-shaped partitioned platform 2 and in a corresponding position(s) in the textile, if the test textile is a quilt, three sleep temperature and humidity sensors 8 are preferably placed on each of an outer side and an inner side of the quilt on the bed-shaped partitioned platform 2. One of the sleep temperature and humidity sensors 8 is located in a middle line, and the other two are located at 20 cm from the middle line; and inside and outside sensors 18 are in one-to-one correspondence in position, and there are 18 temperature and humidity sensors 18 in total.

S3, arranging a physiological index sensor 51 and an acceleration sensor 52 on the body of a subject.

S4, setting and adjusting a controllable temperature and humidity test chamber 1 and the bed-shaped partitioned platform 2 to a pre-set temperature and humidity, and then allowing the experimental subject to enter the controllable temperature and humidity test chamber 1, and the preset temperature and humidity can be set to different values according to different experimental requirements.

S5, completing a heat and humidity comfort level psychological evaluation questionnaire and then allowing the subject to lie on the bed-shaped partitioned platform 2 and entering a sleep state.

S6, monitoring the sleep state of the subject all night and collecting data.

S7, the subject filling in the heat and humidity comfort level psychological evaluation questionnaire and a sleep quality psychological evaluation questionnaire after a pre-determined time period.

S8, analyzing the data obtained from performing the previous steps, and subjectively and objectively evaluating the test textile.

Step S8 further comprises the sub-steps of:

S81, evaluating a heat and humidity transfer performance and a material uniformity of the test textile according to physical level data obtained by the one or more sleep temperature and humidity sensors 8, thereby evaluating an objective heat and humidity comfort level of the test textile;

S82, evaluating a subjective heat comfort level of the test textile according to psychological level data obtained from all questionnaires;

S83, evaluating the sleep quality according to physiological data obtained by the physiological index sensor 51 and the acceleration sensor 52, thereby evaluating the objective heat and humidity comfort level of the test textile; and S84, comprehensively evaluating a sleep heat and humidity comfort level of the test textile according to different data and evaluation results in steps S81, S82 and S83.

For the sub-steps in step S83, steps S81, S82 and S83 can be executed in an arbitrary order.

FIG. 4 is a schematic view of a sensor for collecting physical and physiological data disposed in a micro-environment controllable temperature and humidity method for evaluating heat and humidity comfort level of textiles according to the present disclosure. As shown in FIG. 4, a plurality of physiological index sensors 51 are arranged on the hand, head and face of the subject, and electroencephalography, electrooculogram, electromyography and blood oxygen saturation can be obtained according to the physiological index sensors 51. These pieces of information are used to analyze important sleep quality indexes, such as awake and sleep stage percentage, sleep latency, sleep efficiency (SE), wake after sleep onset (WASO), and arousal times. The sensor connection position and sleep stage evaluation preferably refer to "The AASM Manual for the Scoring of Sleep and Associated Events" published by the American Academy of Sleep Medicine.

The acceleration sensor 52 is placed on the center line of pajama trousers of the subject for collecting data of the body position and activity amount associated with a change of body position of the human body during sleep and using the data of activity amount to help analyze the sleep stage and the sleep quality.

In addition, importantly, it is required to ensure that the subject does not have sleep or the other physical and psychological diseases, and cannot have behaviours such as smoking, drinking, taking prescription drugs, sleeping during daytime, drinking caffeine drinks and dieting within 30 days of the experiment so as to prevent adverse or negative effects on the sleep experiment. Preferably, the subject may pre-sleep for a few nights in the test chamber prior to the experiment, so as to adapt to the environment of the test chamber and reduce the impact of an environmental change on sleep.

I. Physical Testing

Embodiment 1

Textile samples: A is a gauze and pure cotton summer quilt, and B is a multi-layer gauze summer quilt. The test method is as follows:

replacing an original quilt on the bed-shaped test platform with the summer quilt, and placing three temperature and humidity sensors at each of an outer side and an inner side of a mattress above each test platform partition. One of the sensors is located in a middle line, and the other two are located at 20 cm from the middle line, inside and outside sensors are in one-to-one correspondence in position, and there are 18 sensors with the collection of temperature and humidity sensor data being set of a high precision. The temperature of the temperature and humidity test chamber is set to 25° C., with the relative humidity being 65%, and the temperature of the bed-shaped test platform is set to 33° C., with the relative humidity being 55%. Such temperature and humidity are optimal human body sleep temperature and humidity conditions obtained based on some preliminary experiments of the system of the present disclosure. The test time is 30 minutes, and after balance, the data during last ten minutes is taken for analysis; and after the data analysis, the result appears that the moisture permeability of the multi-layer gauze summer quilt is superior to that of the gauze and pure cotton summer quilt, while the thermal insulation property of the gauze and pure cotton summer quilt is superior to that of the multi-layer gauze summer quilt, which is as shown in Table 1 below.

TABLE 1

| Test samples | Difference between temperatures inside and outside the quilt (inside-outside) | Difference between humidity inside and outside the quilt (inside-outside) |
|---|---|---|
| A: gauze and pure cotton summer quilt | 1.5580 ± 0.2302° C. | −10.44 ± 1.61% |
| B: multi-layer gauze summer quilt | 1.1342 ± 0.3557° C. | −8.68 ± 4.64% |

II. Human Test

Embodiment 2

Textile samples: pure cotton quilt cover A and pure cotton quilt cover B The test takes two nights and one sample is tested during one night. The pure cotton quilt cover to be tested is placed over the quilt of the corresponding size of the bed-shaped partitioned platform 2, the temperature of the temperature and humidity test chamber is preset to 25° C., with the relative humidity being 65%, and the temperature of the bed-shaped test platform is preset to 33° C., with the relative humidity being 55%. Such temperature and humidity are optimal human body sleep temperature and humidity conditions obtained based on some preliminary experiments of the system of the present disclosure. Three groups of sleep temperature and humidity sensors 8 are placed respectively under a bed sheet at the location of chest, crotch and feet and inside the quilt; there are 12 temperature and humidity sensors in total, and arrange the physiological index sensor 51 and the acceleration sensor 52 on the experimental subject; and after the test chamber and the bed-shaped partitioned platform reach and are stabilized at a pre-set temperature and humidity, the experimental subject enters the test chamber. The experimental subject lies on the test platform and fills in a heat and humidity comfort level psychological evaluation questionnaire. After the sleep monitoring all night, the experimental subject gets up and fills in the heat and humidity comfort level psychological evaluation questionnaire and a sleep quality psychological evaluation questionnaire.

The data from the sleep temperature and humidity sensor 8 is analyzed, and the result thereof is as shown in Table 2 below.

TABLE 2

| Test samples | Temperature mean | Relative humidity mean |
| --- | --- | --- |
| Pure cotton quilt cover A | 31.97 ± 2.86° C. | 59.7 ± 5.4% |
| Pure cotton quilt cover B | 32.80 ± 2.13° C. | 62.2 ± 3.9% |

The data from the physiological index sensor 51 is analyzed, and the result thereof is as shown in Table 3 below.

TABLE 3

| Test samples | Sleep duration | Sleep efficiency | Sleep latency | Deep sleep percentage | Wake after sleep onset | Arousal times |
| --- | --- | --- | --- | --- | --- | --- |
| Pure cotton quilt cover A | 410 mins | 96.4% | 3 mins | 15% | 9.0 mins | 8 |
| Pure cotton quilt cover B | 412 mins | 96.3% | 4 mins | 17% | 4.5 mins | 5 |

In addition, the data from the acceleration sensor 52 is analyzed, and the result thereof is as shown in Table 4 below.

TABLE 4

| Test samples | Number of times of posture changes |
| --- | --- |
| Pure cotton quilt cover A | 13 |
| Pure cotton quilt cover B | 10 |

The evaluation criteria for the heat and humidity comfort level psychological evaluation questionnaire is as shown in FIG. 5.

The result of the heat and humidity comfort level psychological evaluation questionnaire is as shown in Table 5 below.

TABLE 5

| | Pure cotton quilt cover A | | Pure cotton quilt cover B | |
| --- | --- | --- | --- | --- |
| Test samples | Before sleep | After getting up | Before sleep | After getting up |
| Temperature comfort level | 4 | 5 | 4 | 4 |
| Humidity comfort level | 4 | 4 | 4 | 4 |
| Overall comfort level | 6 | 5 | 6 | 6 |

The result of the sleep quality psychological evaluation questionnaire is as shown in Table 6 below.

TABLE 6

| Test samples | Drowsiness after getting up | Sleep smoothness after falling asleep | Dreaming | Tiredness recovery |
| --- | --- | --- | --- | --- |
| Pure cotton quilt cover A | 18.0 | 29.6 | 29.5 | 15.7 |
| Pure cotton quilt cover B | 23.3 | 22.8 | 29.5 | 15.7 |

From the above-mentioned instances, it can be concluded that pure cotton quilt cover B can provide a better sleep comfort and is superior to pure cotton quilt cover A.

Embodiment 3

Textile Samples: Warm Cotton Pajama Trousers a and Pure Cotton Pajama Trousers B The test needs to take two nights and one sample is tested during one night. The experimental subject wears a pure cotton short sleeve shirt, and the trousers are a sample to be tested. The temperature of the temperature and humidity test chamber is preset to be 25° C., with the relative humidity being 65%, the temperature of a chest section of the bed-shaped partitioned platform is preset to be 33° C., with the relative humidity being 55%, and the temperatures of a crotch section and a lower limb section are preset to be 25° C., with the relative humidity being 65%. Three groups of sleep temperature and humidity sensors 8 are placed respectively at an outer side of pajamas at the location of crotch, knee and feet and inside the quilt, and the positions thereof are in one-to-one correspondence; and there are 12 sleep temperature and humidity sensors 8 in total. The physiological index sensor 51 and the acceleration sensor 52 are arranged on the body of the experimental subject. After the temperature and humidity test chamber 1 and the bed-shaped partitioned platform 2 reach and are stabilized at a pre-set temperature and humidity, the subject enters the test chamber. The subject lies on the test platform and fills in a heat and humidity comfort level psychological evaluation questionnaire. After the sleep monitoring all night, the subject gets up and fills in the heat and humidity comfort level psychological evaluation questionnaire and a sleep quality psychological evaluation questionnaire.

The data from the sleep temperature and humidity sensor 8 is analyzed, and the result thereof is as shown in Table 7 below.

TABLE 7

| Test samples | Temperature mean | Relative humidity mean |
| --- | --- | --- |
| Warm cotton pajama trousers A | 27.53 ± 2.62° C. | 66.4 ± 3.9% |
| Pure cotton pajama trousers B | 28.31 ± 3.01° C. | 65.2 ± 4.7% |

The data from the physiological index sensor 51 is analyzed, and the result thereof is as shown in Table 8 below.

TABLE 8

| Test samples | Sleep duration | Sleep efficiency | Sleep latency | Deep sleep percentage | Wake after sleep onset | Arousal times |
|---|---|---|---|---|---|---|
| Warm cotton pajama trousers A | 433.5 mins | 95.8% | 6.0 mins | 13% | 43.0 mins | 38 |
| Pure cotton pajama trousers B | 467.5 mins | 88.5% | 1.0 min | 10% | 12.0 mins | 11 |

In addition, the data from the acceleration sensor 52 is analyzed, and the result thereof is as shown in Table 9 below.

TABLE 9

| Test samples | Number of times of posture changes |
|---|---|
| Warm cotton pajama trousers A | 13 |
| Pure cotton pajama trousers B | 8 |

The evaluation criteria for the heat and humidity comfort level psychological evaluation questionnaire is as shown in FIG. 5

The result of the heat and humidity comfort level psychological evaluation questionnaire is as shown in Table 10 below.

TABLE 10

| | Warm cotton pajama trousers A | | Pure cotton pajama trousers B | |
|---|---|---|---|---|
| Test samples | Before sleep | After getting up | Before sleep | After getting up |
| Temperature comfort level of lower limbs | 4 | 4 | 4 | 5 |
| Humidity comfort level of lower limbs | 4 | 4 | 4 | 4 |
| Overall comfort level of lower limbs | 5 | 6 | 5 | 5 |

The result of the sleep quality psychological evaluation questionnaire is as shown in Table 11 below.

TABLE 11

| Test samples | Drowsiness after getting up | Sleep smoothness after falling asleep | Dreaming | Tiredness recovery |
|---|---|---|---|---|
| Warm cotton pajama trousers A | 21.0 | 21.1 | 23.3 | 20.8 |
| Pure cotton pajama trousers B | 20.8 | 23.0 | 26.2 | 23.6 |

From the above-mentioned instances, it can be concluded, by means of analysis, that warm cotton pajama trousers A can provide a better sleep comfort and are superior to pure cotton pajama trousers B. It can be seen from the different embodiments above that the method of the present disclosure evaluates the sleep heat and humidity comfort level of textiles in three levels of physics, physiology and psychology, and performs subjective and objective test evaluations on the textiles, thereby making up for the defects in the existing methods that the sleep heat and humidity comfort level of textiles cannot be comprehensively evaluated.

The embodiments of the present disclosure are described above in conjunction with the drawings; however, the present disclosure is not limited to the specific embodiments above, and the above-mentioned embodiments are merely illustrative and not restrictive. Many forms may also be made, with the inspiration from the present disclosure, by those skilled in the art without departing from the spirit of the present disclosure and the scope of the claims, and are all within the protection of the present disclosure.

The invention claimed is:

1. A system for evaluating heat and humidity comfort level of textiles proximal a subject during sleeping, comprising:
   a bed-shaped partitioned platform (2) comprising one or more non-temperature and humidity-controllable sections (21) and one or more temperature and humidity controllable sections (22) which define a micro environment therein;
   one or more temperature and humidity control machines (3) in communication with the one or more temperature and humidity control sections (22) respectively for supplying air with pre-set temperature and humidity; and
   a central controller (4) electrically connected to the one or more temperature and humidity control machines (3); and
   a controllable temperature and humidity test chamber (1), wherein an air outlet (12) and an air return inlet (13) are respectively arranged at the top and bottom of the controllable temperature and humidity test chamber (1), and a diffuser plate (11) is mounted below the air outlet (12); and
   the bed-shaped partitioned platform (2) is arranged in the controllable temperature and humidity test chamber (1), and the air return inlet (13) is further arranged at the bottom of the bed-shaped partitioned platform (2).

2. The system for evaluating heat and humidity comfort level of textiles proximal a subject during sleeping according to claim 1, further comprising:
   a heat and humidity comfort level detection sensing apparatus (5) comprising a physiological index sensor (51) for collecting physiological data, and an acceleration sensor (52) for collecting data of a body position of the subject and an activity amount associated with a change of body position of the subject during sleep on the platform; and one or more sleep temperature and humidity sensors (8) for collecting the micro-environment temperature and humidity of various parts of the subject during sleep.

3. The micro-environment controllable temperature and humidity system for evaluating heat and humidity comfort level of textiles proximal a subject during sleeping according to claim 1, further comprising a test chamber temperature and humidity control machine (6) electrically connected to the central controller (4), wherein air emitted from the test chamber temperature and humidity control machine (6) passes through the air outlet (12) and then enters the controllable temperature and humidity test chamber (1) through the diffuser plate (11).

4. The micro-environment controllable temperature and humidity system for evaluating heat and humidity comfort level of textiles proximal a subject during sleeping according to claim 3, wherein a test chamber temperature and humidity sensor (62) is further arranged at the air outlet (12), and the test chamber temperature and humidity sensor (62) is electrically connected to the central controller (4).

5. The micro-environment controllable temperature and humidity system for evaluating heat and humidity comfort level of textiles proximal a subject during sleeping according to claim 3, wherein the one or more temperature and humidity control machines (3) are respectively in communication with one or more ventilation pipelines (31), and air outlets of the one or more ventilation pipelines (31) respectively correspond to and are in communication with one or more lower-layer air inlets (23) arranged at the bottom of the bed-shaped partitioned platform (2), and the one or more lower-layer air inlets (23) are respectively in communication with one or more section diffusers (24) arranged thereabove; and a heat dissipation polyester layer (25) is arranged close to and above the one or more section diffusers (24), an upper-layer return air passage (26) is arranged above the heat dissipation polyester layer (25), and the upper-layer return air passage (26) is in communication with the controllable temperature and humidity test chamber (1).

6. The micro-environment controllable temperature and humidity system for evaluating heat and humidity comfort level of textiles proximal a subject during sleeping according to claim 5, wherein air inlets of the one or more ventilation pipelines (31) are respectively provided with one or more temperature sensors (32), and the one or more temperature sensors (32) are respectively electrically connected to the central controller (4).

7. The micro-environment controllable temperature and humidity system for evaluating heat and humidity comfort level of textiles proximal a subject during sleeping according to claim 1, wherein a connection opening (14) is arranged on a side wall of the controllable temperature and humidity test chamber (1), and data cables of the physiological index sensor (51) and the acceleration sensor (52) are connected to an external computer through the connection opening (14); and a ventilation window (15) is further arranged on the side wall of the controllable temperature and humidity test chamber (1), and a ventilation fan (16) is arranged in the ventilation window (15).

8. A micro-environment controllable temperature and humidity method for evaluating heat and humidity comfort level of textiles proximal a subject during sleeping, comprising:

disposing a test textile on a bed-shaped partitioned platform (2);

arranging one or more sleep temperature and humidity sensors (8) respectively under the surface of a mattress (29) of the bed-shaped partitioned platform (2) and in a corresponding position in the textile;

arranging a physiological index sensor (51) and an acceleration sensor (52) on the body of a subject;

setting and adjusting a controllable temperature and humidity test chamber (1) and the bed-shaped partitioned platform (2) to the same pre-set temperature and humidity, and then allowing the subject to enter the controllable temperature and humidity test chamber (1);

receiving a completed heat and humidity comfort level psychological evaluation questionnaire from the subject and thereafter allowing the subject to lie on the bed-shaped partitioned platform (2) and entering a sleep state;

monitoring the sleep state of the subject all night and collecting data;

receiving a further heat and humidity comfort level psychological evaluation questionnaire and a sleep quality psychological evaluation questionnaire after a predetermined time period from the subject; and analyzing the data obtained from performing the previous steps, and subjectively and objectively evaluating the test textile.

9. The micro-environment controllable temperature and humidity method for evaluating heat and humidity comfort level of textiles proximal a subject during sleeping according to claim 8, the analyzing data and evaluating the test textile further comprises:

evaluating a heat and humidity transfer performance and a material uniformity of the test textile according to physical level data obtained by the one or more sleep temperature and humidity sensors (8), thereby evaluating an objective heat and humidity comfort level of the test textile;

evaluating a subjective heat comfort level of the test textile according to psychological level data obtained from all the questionnaires;

evaluating the sleep quality according to physiological data obtained by the physiological index sensor (51) and the acceleration sensor (52), thereby evaluating the objective heat and humidity comfort level of the test textile; and comprehensively evaluating a sleep heat and humidity comfort level of the test textile according to different data and evaluation results in the previous steps, wherein the steps before comprehensively evaluating are executed in an arbitrary order.

\* \* \* \* \*